(12) United States Patent
Bakalyar et al.

(10) Patent No.: US 6,728,333 B2
(45) Date of Patent: Apr. 27, 2004

(54) FILM DENSITY TEMPLATE AND METHOD FOR COMPARISON OF FILM EXPOSURE

(75) Inventors: Donovan M. Bakalyar, Dearborn, MI (US); Lance Hefner, Troy, MI (US)

(73) Assignee: William Beaumont Hospital, Royal Oak, MI (US)

( * ) Notice: Subject to any disclaimer, the term of this patent is extended or adjusted under 35 U.S.C. 154(b) by 56 days.

(21) Appl. No.: 10/124,924

(22) Filed: Apr. 18, 2002

(65) Prior Publication Data

US 2002/0172325 A1 Nov. 21, 2002

Related U.S. Application Data

(60) Provisional application No. 60/284,682, filed on Apr. 18, 2001.

(51) Int. Cl.⁷ .............................................. G01N 23/04
(52) U.S. Cl. ........................................... 378/62; 378/37
(58) Field of Search ..................... 378/37, 62, 207, 378/162, 165; 250/252.1

(56) References Cited

U.S. PATENT DOCUMENTS

| | | | |
|---|---|---|---|
| 4,759,045 A | 7/1988 | Lasky | 378/37 |
| 5,063,583 A | 11/1991 | Galkin | 378/207 |
| 5,276,726 A | 1/1994 | Galkin | 378/207 |
| 5,406,612 A | 4/1995 | Galkin | 378/207 |
| 5,544,238 A | 8/1996 | Galkin | 378/207 |
| 5,565,678 A | 10/1996 | Galkin | 250/252.1 |
| 5,844,965 A | 12/1998 | Galkin | 378/207 |

Primary Examiner—David V. Bruce
Assistant Examiner—Courtney Thomas
(74) Attorney, Agent, or Firm—Brinks Hofer Gilson & Lione (57) ABSTRACT

The present invention provides an apparatus and method permitting one sheet of radiographic film to be exposed multiple times including a control unit for correcting the optical density of the film based upon the spatial variation of x-ray field intensity. In particular, the present invention includes a system and method for determining an optical density of radiographic imaging film utilizing a mask for absorbing soft x-ray radiation thereby creating a reference exposure, and further utilizing a template to execute a number of sequential exposures of radiographic imaging film such that the radiographic film is selectively irradiated. The control unit is adapted for deriving a corrective optical density value based upon reference measurements, and correcting the series of template exposures using the corrective optical density value.

12 Claims, 6 Drawing Sheets

FILM DENSITY TEMPLATE AND METHOD FOR COMPARISON OF FILM EXPOSURE

CROSS-REFERENCE TO RELATED APPLICATIONS

This application claims the benefit of U.S. Provisional Application No. 60/284,682 filed on Apr. 18, 2001.

BACKGROUND OF THE INVENTION

1. Field of the Invention

The present invention relates to the field of radiographic imaging, and in particular, to methods and apparatus for determining the optical density of radiographic imaging film and further enacting corrective adjustments to the optical density of radiographic imaging film used, for example, in mammography.

2. Description of Prior Art

Radiographic imaging of body parts is well known and extremely useful as a diagnostic tool in the medical arts. Radiographic imaging involves positioning a part of a patient to be imaged denoted as the "structure of interest" under an x-ray emitter, exposing the structure of interest to an x-ray beam, and recording the interaction between the x-ray beam and the structure of interest on an image receptor. In most cases, the receptor is radiographic film, and the image is amplified by an intensifying screen. After exposing the structure of interest, the film is removed from the cassette and then developed.

The diagnostic value of radiographic imaging as described is dependent upon the interplay of several factors. One of the most important of these factors is the optical density of the radiographic film. In order to ensure optimal film exposure, typical imaging devices implement an automatic exposure control system (AEC). A typical AEC utilizes a radiation detector for detecting the amount of radiation. The radiation detector is generally disposed adjacent to the radiographic film such that the radiation impinges upon the detector prior to irradiating the radiographic film. In general, the typical energy per photon of the x-ray is sufficient to render the detector transparent or invisible on the radiographic film. Thereafter, the AEC utilizes algorithms and lookup tables to account for the varying properties of the intensifying screen, the radiographic film, and the processor. The AEC then makes the necessary adjustments to the intensity and duration of the radiation. Thus, the AEC is essentially a closed-loop feedback mechanism for optimizing the quality of radiographic images.

Although an AEC is generally sufficient for a standard imaging device, mammography machines present additional problems. First and foremost among these problems is that the typical energy per photon of the x-radiation emitted by a mammography machine is far less than that of other types of imaging devices. Mammography machines emit so-called "soft" x-rays that are optimal for detecting subtle differences in the soft tissue found in the human breast. However, soft x-rays present a limitation in that they cannot be transmitted through the radiation detector without imaging parts of the detector on the radiographic film. Thus, the detector must be disposed such that the radiographic film is irradiated prior to detection of the amount of radiation impinging upon the film. As a result, the detector will detect amounts of radiation that can be significantly less than what has irradiated the film. Consequently, the reliability of an AEC is slightly compromised when used in a mammography machine.

Consequently, each mammography machine must have the AEC system frequently calibrated and adjusted on site by a service engineer. The process of calibration is tedious and expensive for many reasons. First, each cassette is slightly different, and thus, the same cassette must be used for multiple exposures. Secondly, radiographic films must be used from the same box to maximize the homogeneity of the film. Thirdly, significant variations can arise in the processor including chemical variation and temperature variation.

Thus, there is a need in the art for an apparatus and method that permit one sheet of radiographic film to be exposed multiple times including a simple and reliable method for determining the optical density of the film. However, such a solution must account for the decrease in the intensity of the x-ray field with an increase in distance from the source, known as the inverse square law. Optical density is also dependent upon the intensity of the x-ray field, such that there is additionally a need for an apparatus and method that compensates optical density measurements for changes due to the spatial variation.

SUMMARY OF THE PRESENT INVENTION

The present invention provides an apparatus and method permitting one sheet of radiographic film to be exposed multiple times including a control unit for correcting the optical density of the film based upon the spatial variation of x-ray field intensity. In particular, the present invention includes a system for determining an optical density of radiographic imaging film comprising an emitter of soft x-ray radiation, a sheet of radiographic imaging film disposed a distance from the emitter, an attenuator simulating the radiological properties of a human breast, a mask for absorbing soft x-ray radiation disposed between the attenuator and the radiographic imaging film thereby creating a reference exposure, and a template for selectively irradiating the radiographic film.

The combination of the foregoing elements allows for multiple exposures on a single sheet of radiographic film. The mask defines a divide along its central axis that is coincident with the center portion of the film, thereby allowing the center portion of the film to be exposed during a reference exposure. The mask prohibits the exposure of two portions of the film that are laterally adjacent to the divide. The template is then aligned such that it permits selective irradiation of the portion of the film that was previously unexposed, and prohibits exposure of film that is yet to be exposed. The template is then moved such that previously unexposed film may be exposed, and again, the template prohibits exposure of film that is yet to be exposed. The foregoing process is repeated until there are enough sequential exposures to warrant processing the film. The template defines The method of the present invention includes a step of irradiating a single sheet of radiographic film while simultaneously absorbing portions of radiation with a mask thereby preventing exposure of portions of the film. The mask defines a divide along its central portion, which allows the center of the film to be irradiated while preventing other portions from being irradiated. The unexposed portions of the film is selectively exposed multiple times utilizing a template having apertures for transmitting x-radiation such that film exposure occurs at various distances from the center of the film. The multiply and selectively exposed film is interpreted by a densitometer that measures the optical density of the film. The optical density data is corrected by the controller, which corrects the optical density measurements based upon the relationship between the distance between the point of interest and the center of the film.

The above and further objects of the present invention will more fully be apparent from the following detailed description with accompanying drawings.

DETAILED DESCRIPTION OF THE PREFERRED EMBODIMENT

Figure 1:
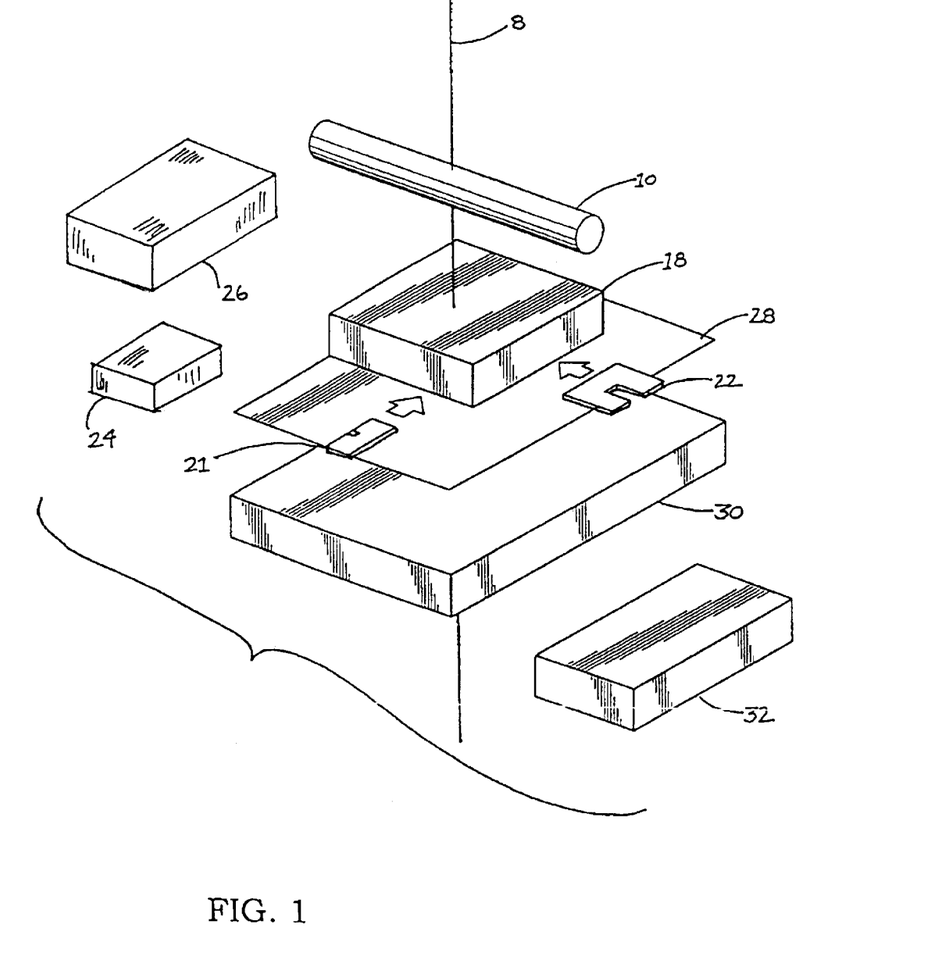
FIG. 1 is an exploded perspective view of the present invention in schematic representation depicting the orientation of the elements.

In accordance with the preferred embodiment of the present invention, FIG. 1 is an exploded schematic diagram of the elements of the present invention. An emitter of soft x-ray radiation 10 of the type commonly used in mammography applications is utilized as a source for x-ray beams (not shown). Emitter 10 is disposed a distance from a surface of a sheet of radiographic film 28 that is normal to axis 8. Radiographic film 28 is of the type that is sensitive to x-ray radiation and, as such, will absorb incident x-ray beams thereby forming an image indicative of the optical density of radiographic film 28, as discussed further herein.

An attenuator 18 is disposed between the emitter 10 and the radiographic film 28 such that x-ray beams are transmitted through attenuator 18 prior to irradiating radiographic film 28. Attenuator 18 is a homogeneous material, such as BR-12 or acrylic plastic, which simulates the density and radiological properties of the human breast.

A mask 22 and a template 21 are sequentially disposed between attenuator 18 and radiographic film 28. Mask 22 and template absorb x-ray beams thereby preventing x-ray beams from irradiating portions of radiographic film 28 and permitting multiple exposures of the radiographic film. The specific designs of mask 22 and template 21 are discussed further herein.

A table 30 is commonly used as a support structure for a mammography machine. In a typical mammography machine, the table 30 will house a cassette (not shown) for housing radiographic film 28 and will be utilized by medical staff to ensure the proper placement and alignment of the structure of interest. In FIG. 1, the table 30 is shown as supporting radiographic film 28.

Multiply exposed radiographic film 28 is generally processed in a processor 32, which is adapted for processing the radiographic film 28 such that an image of the structure of interest is shown in gray scale.

A densitometer 24 of the type commonly used in mammography application is utilized for detecting levels of a gray scale formed upon radiographic film 28, and is further adapted for determining an optical density of radiographic film 28.

A controller 26 is utilized for processing optical density data determined by the densitometer 24. The controller 26 is adapted for correcting the optical density data and determining a corrective optical density as discussed further herein.

Figure 2:
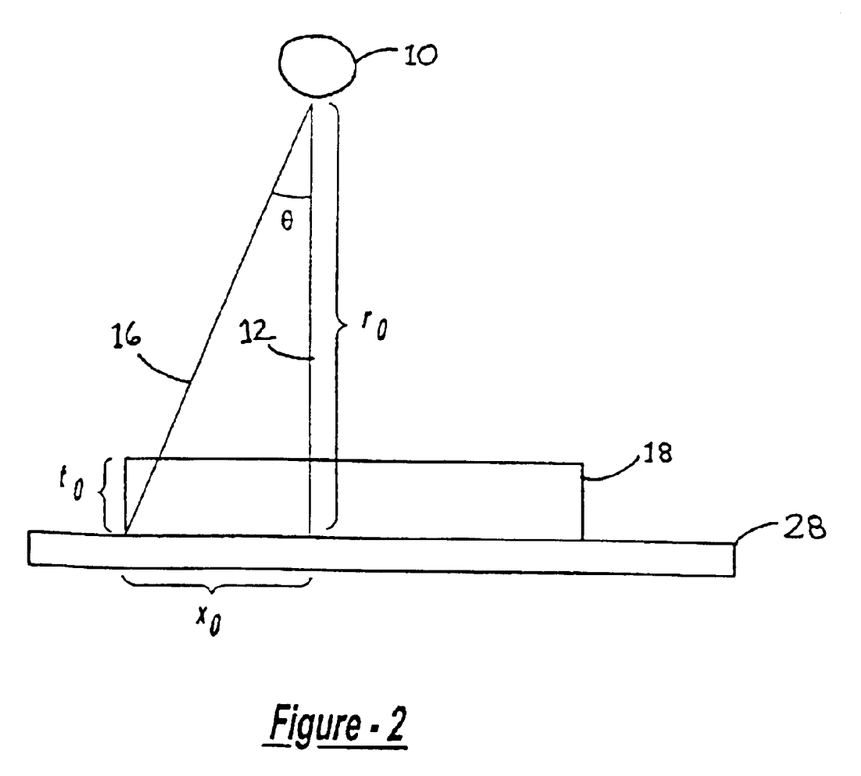
FIG. 2 is a schematic depiction of the components of the present invention including the relevant dimensions of the present invention.

FIG. 2 depicts the relevant geometrical dimensions of the present invention. The distance from the emitter 10 to the radiographic film 28 is $r_o$. An x-ray beam 12 emitted along axis 8 will travel distance $r_o$ and orthogonally impinge upon radiographic film 28 at a point $x_o$. X-ray beam 16 is emitted from emitter 10 at an angle θ from axis 8, and will impinge upon radiographic film 28 at an angle equal to the difference between ninety degrees and θ. The point at which x-ray beam 16 impinges upon radiographic film 28 is a distance x from the point $x_o$. In determining a corrected optical density, the controller will arbitrarily assign the point $x_o$ a value of zero. Additionally, FIG. 2 depicts attenuator 18 as having a thickness $t_o$ through which x-ray beams 12, 16 must pass before impinging upon radiographic film 28.

Figure 3:
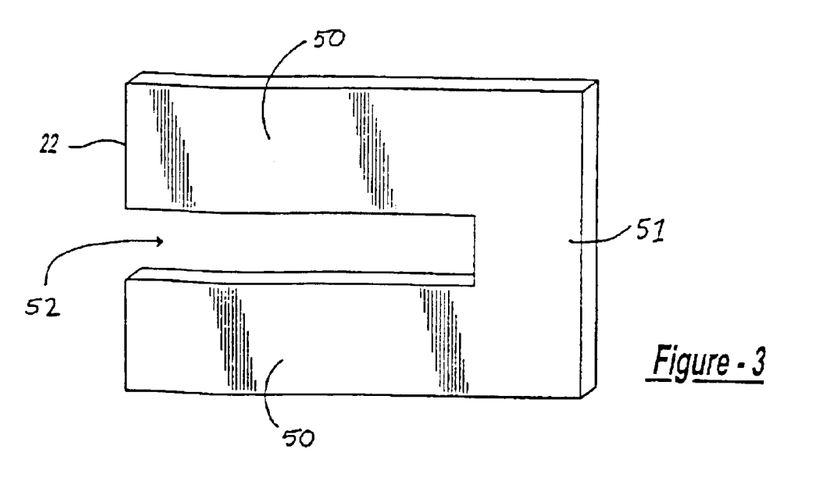
FIG. 3 depicts a masking element of the type used in the present invention.

FIG. 3 is a preferred profile of the mask 22 that is disposed between the attenuator 18 and the radiographic film 28 for absorbing x-ray radiation. The mask 22 defines a center portion 51, two lateral portions 50, and a divide 52. Center portion 51 and lateral portions 50 prohibit the transmission of x-ray radiation, thereby preventing exposure of portions of radiographic film coincident therewith. Divide 52 permits the transmission of x-ray radiation, and radiographic film coincident therewith may be exposed.

Figure 4:
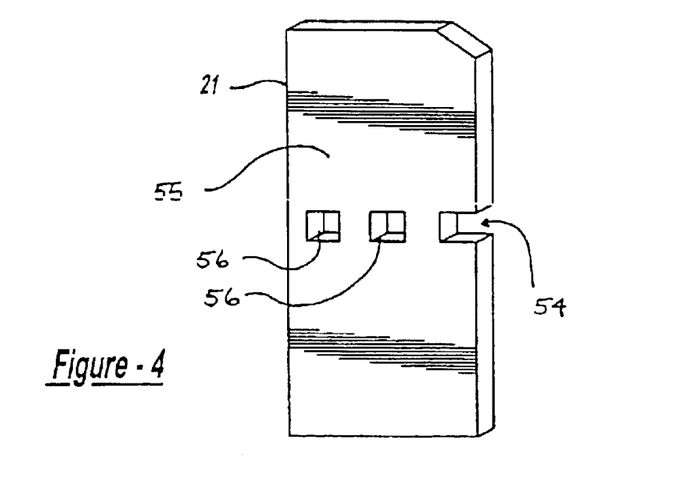
FIG. 4 depicts a template of the type used in the present invention.

FIG. 4 is a preferred profile of the template 21 that is selectively disposed between attenuator 18 and radiographic film 28 in order to selectively permit irradiation of radiological film 28. Template 21 defines body portion 55 that prohibits the transmission of x-ray radiation thereby preventing exposure of portions of radiographic film coincident therewith. Template 21 further defines a pair of apertures 56 disposed within body portion 55 that permit the transmission of x-ray radiation. Template 21 further defines an open aperture 54 that is square in shape and that has one side coincident with an edge of the template 21, thereby forming an open aperture.

Figure 5:
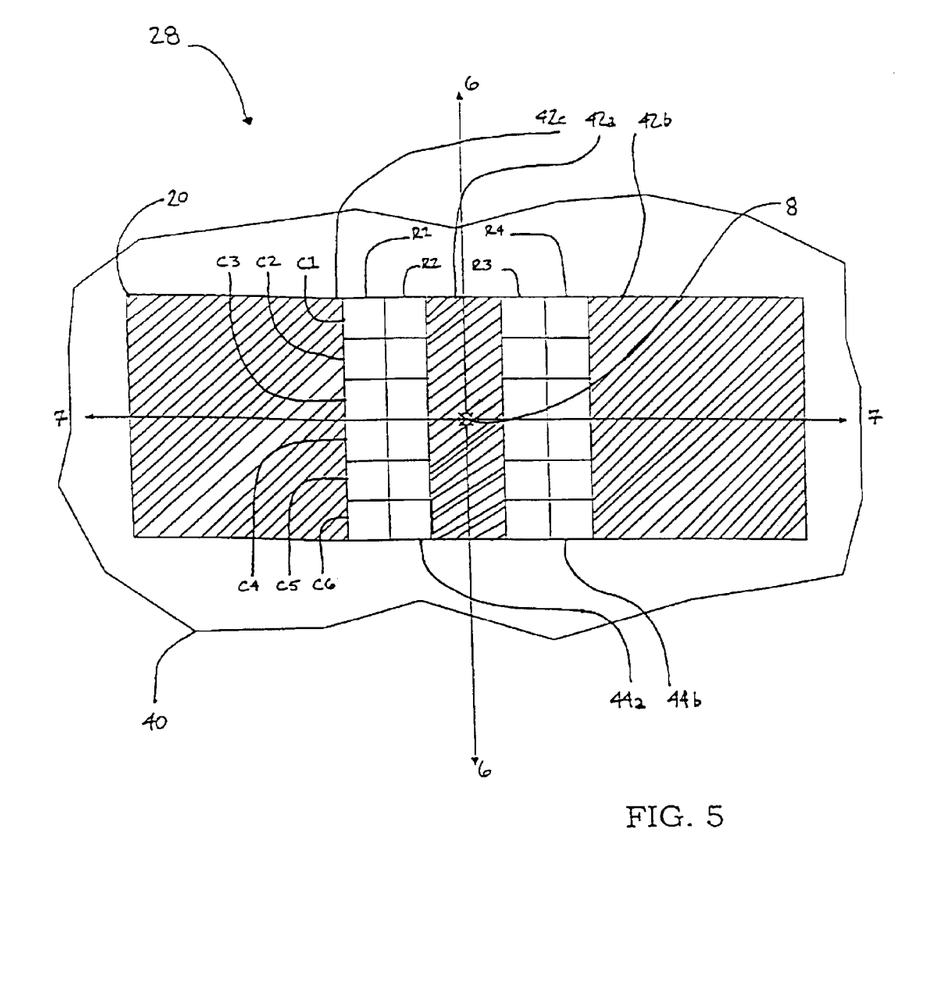
FIG. 5 is a schematic view of a sheet of radiological film that has been shielded by a mask and been exposed multiple times while employing a template to form a grid of exposures along two portions of film adjacent to the center of the film.

FIG. 5 is a schematic view of a sheet of radiographic film 28 having an image 20 irradiated on it by x-rays and having been exposed multiple times utilizing the mask 22 and template 21 of the present invention. An axis 6 is shown perpendicular to an axis 7. Axes 6 and 7 intersect at a point where axis 8 intersects radiographic film. In a typical mammography machine, the shoulders of a patient are perpendicular to vertical axis 6 and parallel to horizontal axis 7.

The fringe area 40 of the radiographic film 28 has been exposed multiple times, and is generally not considered in the calibration procedure or in measuring optical density.

Reference areas include a central portion 42a, a lateral portion 42b, and a lateral portion 42c. Reference areas 42a, 42b, and 42c are created in a reference exposure when the mask depicted in FIG. 3 is disposed between attenuator 18 and radiographic film 28 and x-rays are emitted from emitter 10.

Template areas 44a, 44b are adjacent to mask area 42a and are generally rectangular in nature such that axis 7 bisects both template areas 44a, 44b. Template areas 44a, 44b can be further described by referring to a grid pattern. In the preferred embodiment, template areas 44a, 44b include columns C1, C2, C3, C4, C5, and C6 as well as rows R1, R2, R3, and R4. Thus, any grid point in template areas 44a, 44b can be referred to as a combination of a row coordinate and a column coordinate.

Figure 6:
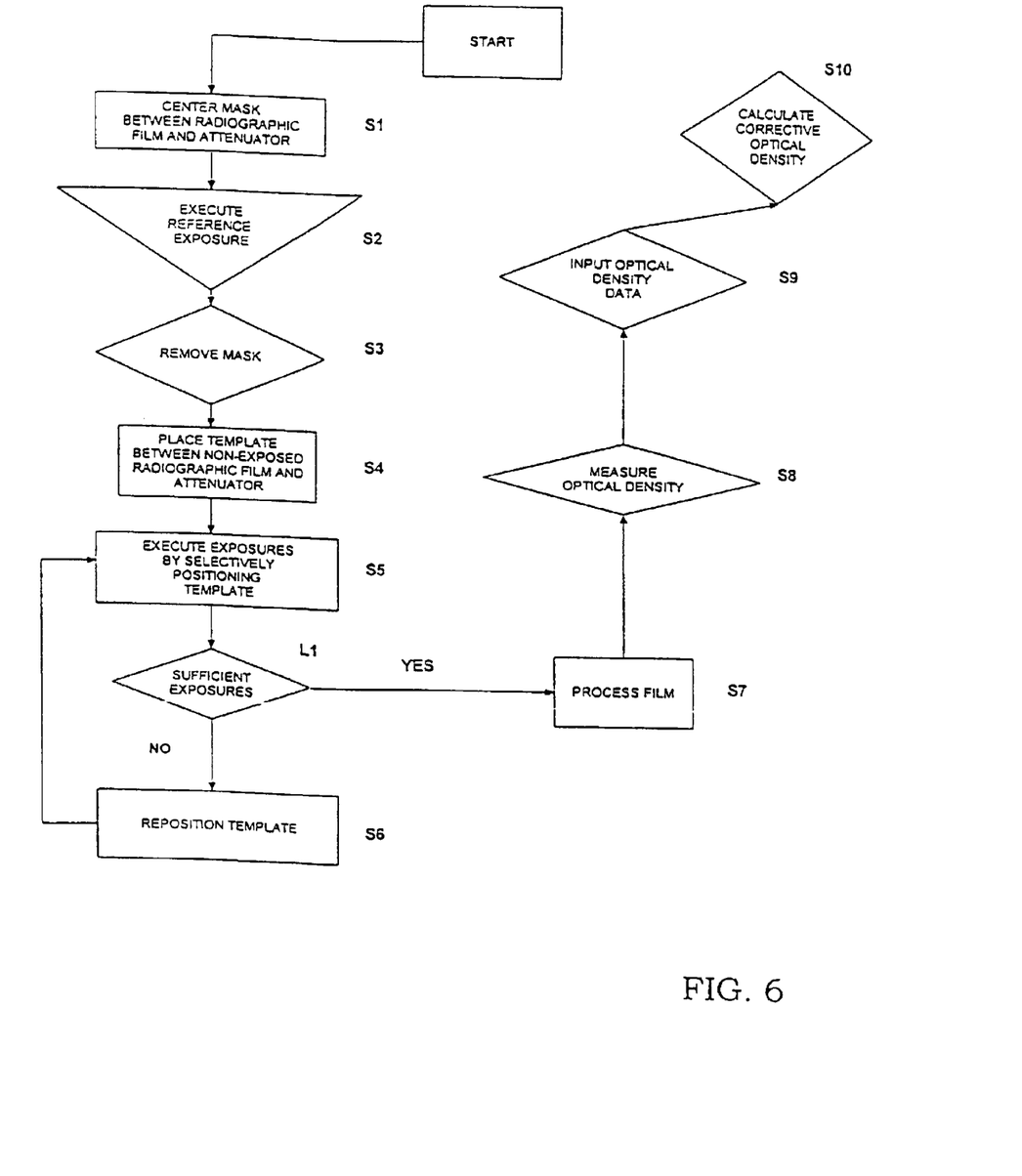
FIG. 6 is a flow chart illustrating the method of the present invention.

Referring now to FIG. 6, a flow chart of the describing the system and method of the present invention. In step S1, the mask 22 is centered on radiographic film 28 such that divide 52 is bisected by axis 6 and such that center portion 51 is parallel to axis 7. Step S1 also includes placing the attenuator 18 over mask 22 such that the x-rays are attenuated before irradiating the mask 22 and radiographic film 28.

In step S2, a reference exposure is executed wherein fringe area 40, and reference portions 42a, 42b, 43c are initially exposed to x-radiation. Only template areas 44a, 44b remain unexposed. The reference exposure executed in step S3 is for calibrating controller 26. The optical density of reference points located in reference areas 42a, 42b, and 42c is utilized by controller 26 to interpolate a corrective optical density.

In step S3, the mask 22 and attenuator 18 are removed.

In step S4, the template 21 is placed over a template area 44a, 44b and the attenuator 18 is placed thereupon. Step S5 consists of irradiating radiographic film 28 such that template 21 selectively irradiates the film through apertures 54, 56. In step S6, the position of the template 21 is changed relative to template areas 44a, 44b. Step S6 may then proceed to step S7 or loop back to step S5 depending on the outcome of logic gate L1. In the preferred embodiment, step S6 loops back to step S5 until template areas 44a, 44b have been repeatedly exposed to provide sufficient data for an optical density test.

The process of alternating between steps S6 and S5 has many embodiments, and the following description is merely illustrative of one of such embodiments requiring eight iterations through logic gate L1. In a first S5 exposure, the template 21 is aligned such that open aperture 54 coincides with the area designated by C6, R1. In such an alignment, apertures 56 will coincide with the areas designated by C4, R1 and C2, R1 respectively. The exposure of step S5 is then executed, and step S6 is performed.

A representative performance of step S6 is to move template 21 such that open aperture coincides with area C6, R2, and further such that apertures 56 coincide with areas C4, R2, and C2, R2 respectively. The exposure of step S5 is then executed, and step S6 is performed.

Two further iterations of the preceding pattern are performed such that the areas designated by columns C6, C4, and C2 and rows R1, R2, R3, and R4 have all been exposed in a series of four cycles of steps S5 and S6.

A fifth iteration of the procedure includes rotating template 21 about axis 7 such that open aperture 54 is coincident with area C1, R4, and further such that apertures 56 are coincident with areas C3, R4 and C5, R4 respectively. Iterations six, seven, and eight of steps S5 and S6 are performed by repeatedly moving template 21 parallel to axis 7 such that the areas designated by columns C1, C3, and C5 and rows R1, R2, R3, and R4 are exposed sequentially.

Upon sufficient exposure of template areas 44a, 44b, logic gate L1 directs that the radiographic film 28 is processed by film processor 30 as given in step S7. Radiographic film 28 has been exposed nine times and requires processing only once. As noted, this is a principal advantage of the present invention.

In step S8, a densitometer 24 is utilized to measure the optical density of the processed film 20.

In step S9, the optical density data is inputted into controller 26 for correcting. Although many methods of inputting the optical density data are available, in the preferred embodiment, the data is entered manually by a medical physicist or other technician.

In step S10, the controller determines a corrective optical density to correct any aberrations in the optical density data incurred due to the spatial dependence of the x-ray field intensity. In doing so, the controller employs a corrective algorithm corresponding to certain physical and mathematical properties of the mammography process. The controller is adapted to account for the following properties. A distance x is the distance from the point $x_o$ to an exposed point on radiographic film 28; $r_o$ is the distance between the emitter 10 and the radiographic film 10, $\theta$ is the angle between the axis 8 and the path of x-ray beam 16, and $t_o$ is the thickness of attenuator 18. The attenuation coefficient of attenuator 18 is denoted $\alpha$. In general, the attenuation coefficient $\alpha$ varies inversely with the emitter potential of the emitter 10 in kilovolts (kV), such that if the kilovoltage of the emitter 10 is increased, then the attenuation coefficient decreases.

The corrective optical density $\Delta OD$ follows mathematically from the relationships between the foregoing properties. In general, the exposure of the radiographic film is related to the energy deposited by the x-ray beams at the radiographic film 28. The magnitude of the x-ray field strength can be described as a function of the parameter x in the following equation:

$$E(x) = A \frac{e^{-\alpha t(x)}}{x^2 + r^2} \quad (1)$$

where $t(x) = t_o \sec\theta$, and A is a constant proportional to the net charge of the emitter 10 measured in milliAmp seconds (mAs).

The ratio of the x-ray field strength at a point x relative to the point $x_o$ is given by the following equation:

$$\frac{E(x)}{E(0)} = \frac{e^{-\alpha[t(x)-t_0]}}{1+(x/r_o)^2} \quad (2)$$

Assuming that x is much less than $r_o$, equation 2 can be simplified to the relationship shown in the following equation:

$$\frac{E(x)}{E(0)} = \frac{e^{-\frac{\alpha t_o}{2}(x/r_o)^2}}{1+(x/r_o)^2} \quad (3)$$

Note that the foregoing approximation eliminated any need to measure $\theta$, which was the angle between the path of x-ray beam 16 and axis 8. Further approximation using a Taylor expansion yields the change in electric field relative to the electric field at the point $x_o$, or rather $$\frac{\Delta E}{E(0)} \approx \left[1 + \frac{\alpha t_o}{2}\right]\left(\frac{x}{r_o}\right)^2 \quad (4)$$

From empirical analysis, it is realized that $$\partial OD = 1.72\left(\frac{\partial mAs}{mAs}\right) = 1.72\left(\frac{\partial E}{E}\right) \quad (5)$$

Therefore, combining equations (4) and (5) yields the following relationship between $\Delta OD$ and the system constraints:

$$\Delta OD \approx -1.72\left[1 + \frac{\alpha t_0}{2}\right]\left(\frac{x}{r_0}\right)^2 \quad (6)$$

Equation 6 is a quadratic equation in x, or conversely, if x is known, then equation 6 is a quadratic equation for $\Delta OD$. A previously complex formula dependent upon a number of variables is simplified to a quadratic equation that controller 26 may utilize to compute a corrective optical density.

Figure 7:
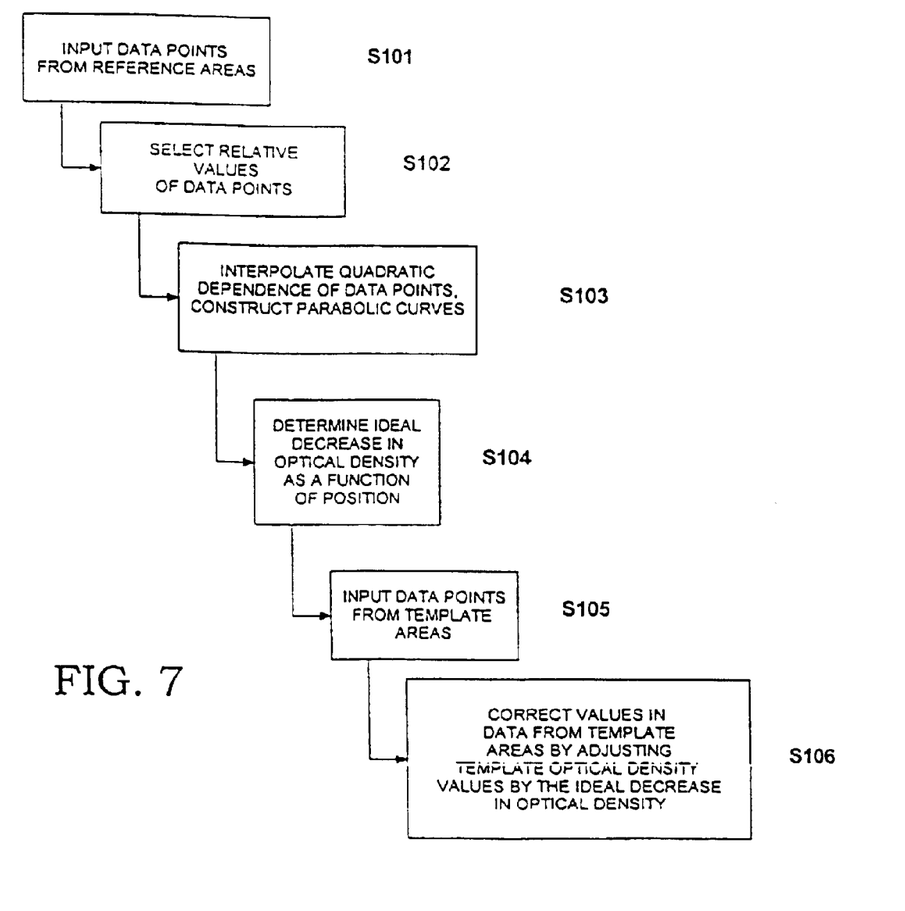
FIG. 7 is a flow chart illustrating the method by which a controller determines a corrective optical density.

FIG. 7 illustrates the method by which controller 26 computes the corrective optical density. Controller 26 fits a minimum of three data points to a parabola by interpolating optical density data measured by the densitometer 24. In the preferred embodiment, controller 26 will select three data points each from reference areas 42a, 42b, and 42c as shown in step S101. The data points will vary in space relative to axes 6 and 7 such that at least three columns of columns C1, C2, C3, C4, C5 and C6 will contain at least three data points.

Given equation 6, it is understood that the optical density should decrease by a certain amount as the distance from the intersection of axes 6, 7, and 8 increases along axis 7. Thus, controller sorts data points relative to their spatial orientation and their relative optical density as shown in step S102. Controller 26 presumes the quadratic form of equation 6, and interpolates reference curves that fit a set of parabolas as shown in step S103. In step S104, the controller 26 determines an actual decrease in optical density. The parabolas obey functions that represent the actual ΔOD of the system, which implicitly contains the properties of the attenuation constant, the attenuator thickness, and the distance from the radiographic film 28 to the emitter 10.

Once the foregoing calibration is completed, then optical density data from a selection of points within template areas 44a, 44b may be selected in accordance with step S105. In step S106, the controller 26 corrects the optical density data from the template areas 44a, 44b by adding a corrective ΔOD as determined from the calibration procedure. Thereafter, the corrected optical density, having been gathered over a series of exposures as determined in FIG. 6, should ideally be representative of the actual optical density of the radiographic film 28.

In calculating a corrective ΔOD, the controller 26 permits a medical physicist or other technician to eliminate the variation of optical density as a function of space. Assuming that the other factors determinative of optical density are constant, any discrepancy between the corrective ΔOD and the reference value determined during calibration may be indicative of machine error. Therefore, the present invention provides an improved system and method for assessing the optical consistency of the mammography machine.

While specific illustrative embodiments of the system and method of the present invention have been disclosed in the foregoing specification, it is understood that various modifications within the scope of the invention may occur to those skilled in the art. For example, alternative profiles of mask 22 and template 21 may be utilized to execute a greater or lesser number of exposures exposing different reference and template areas of radiographic film 28. It is intended, therefore, that all such adaptations and modifications should be comprehended as falling within the scope and meaning of the following claims.

We claim:

1. A system for determining an optical density of radiographic imaging film, said system comprising:
   an emitter of soft x-ray radiation disposed about an axis at a first end;
   a platform disposed about said axis at a second end;
   an attenuator disposed between said emitter and said platform about said axis;
   a radiographic imaging film defining a surface normal to said axis and disposed between said platform and said attenuator;
   a mask for absorbing soft x-ray radiation disposed between said attenuator and said radiographic imaging film during a reference exposure;
   a template disposed between said attenuator and said radiographic imaging film, said template defining at least one aperture for selectively transmitting x-rays through to said radiographic imaging film during at least one template exposure thereby irradiating an exposed area of said radiographic film;
   wherein a predetermined exposure sequence of said at least one template exposure and said reference exposure irradiate said radiographic film such that an optical density measurement of said radiographic film corresponds to a predetermined number of exposures.

2. The system of claim 1 further comprising a controller adapted for calculating a corrective optical density correcting for an aberration in said optical density measurement based in part upon a distance from said axis to said exposed area of radiographic film, and further wherein said controller corrects said aberration in said optical density measurement by utilizing a reference optical density measurement.

3. The system of claim 1 wherein one of said at least one aperture defines a square aperture, wherein one side of said square aperture is coextensive with an edge of said template.

4. The system of claim 1 wherein said at least one aperture is rectangular.

5. The system of claim 1 wherein said mask comprises a first lateral portion coupled to a second lateral portion by a connecting portion, and further wherein said first lateral portion, said second lateral portion and said connecting portion cooperate to define a divide.

6. The system of claim 1 wherein said attenuator is adapted to simulate a plurality of radiological properties of a human breast.

7. The system of claim 1 wherein said attenuator comprises BR-12.

8. The system of claim 1 wherein said controller is adapted for calculating a corrective optical density correcting for aberrations in the optical density based in part on an attenuation coefficient of said attenuator.

9. The system of claim 1 wherein said controller is adapted for calculating a corrective optical density correcting for aberrations in the optical density based in part on a thickness of said attenuator.

10. The system of claim 1 wherein said controller is adapted for calculating a corrective optical density correcting for aberrations in the optical density based in part on a distance between said radiographic film and said emitter.

11. A method for determining an optical density of radiographic imaging film, said method comprising:
   utilizing a mask to irradiate a plurality of reference portions on said radiographic imaging film;
   selectively irradiating radiographic imaging film with soft x-rays utilizing a template thereby forming a plurality of irradiated areas upon said radiographic imaging film;
   moving said template relative to said radiographic imaging film a predetermined number of times such that a predetermined number of areas is selectively irradiated;
   measuring the optical density of said plurality of irradiated areas of said radiographic imaging film;
   correcting measurements of the optical density of said plurality of irradiated areas of said radiographic imaging film based in part upon an aberration in a set of optical density measurements for said plurality of reference areas.

12. The method of claim 11 further comprising the step of attenuating said soft x-rays with an attenuator.

* * * * *